United States Patent
Laakkonen et al.

(10) Patent No.: US 10,834,535 B2
(45) Date of Patent: Nov. 10, 2020

(54) METHOD FOR MONITORING ACTIVITY OF SUBJECT AND MONITORING DEVICE THEREFOR

(71) Applicant: Oura Health Oy, Oulu (FI)

(72) Inventors: Harri Laakkonen, Oulu (FI); Hannu Kinnunen, Oulu (FI)

(73) Assignee: Oura Health Oy, Oulu (FI)

(*) Notice: Subject to any disclaimer, the term of this patent is extended or adjusted under 35 U.S.C. 154(b) by 1238 days.

(21) Appl. No.: 14/953,747

(22) Filed: Nov. 30, 2015

(65) Prior Publication Data

US 2017/0156036 A1   Jun. 1, 2017

(51) Int. Cl.
| | | |
|---|---|---|
| *A61B 5/00* | (2006.01) | |
| *H04W 4/02* | (2018.01) | |
| *A61B 5/06* | (2006.01) | |
| *H04B 1/3827* | (2015.01) | |
| *G01B 11/02* | (2006.01) | |

(52) U.S. Cl.
CPC .............. *H04W 4/027* (2013.01); *A61B 5/06* (2013.01); *A61B 5/684* (2013.01); *A61B 5/6824* (2013.01); *A61B 5/6826* (2013.01); *H04B 1/385* (2013.01); *A61B 5/681* (2013.01); *A61B 2562/0219* (2013.01); *G01B 11/026* (2013.01); *H04B 2001/3861* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,924,907 B2* | 3/2018 | Alberth | ............... | A61B 5/7435 |
| 9,936,912 B2* | 4/2018 | Roovers | ............... | G01C 22/002 |
| 10,254,804 B2* | 4/2019 | Dusan | ................... | G04C 3/002 |

(Continued)

FOREIGN PATENT DOCUMENTS

| | | |
|---|---|---|
| EP | 1271099 A2 | 1/2003 |
| WO | 2014172381 A1 | 10/2014 |

(Continued)

OTHER PUBLICATIONS

International Search Report and Written Opinion of the International Searching Authority, Application No. PCT/FI2016/050807, dated Feb. 27, 2017, 12 pages.

*Primary Examiner* — Michael W Kahelin
*Assistant Examiner* — Shirley X Jian
(74) *Attorney, Agent, or Firm* — Ziegler IP Law Group, LLC

(57) ABSTRACT

Disclosed is a method for monitoring activity of a subject and a monitoring device therefor. The method comprises, detecting the direction of the monitoring device with respect to a hand of a subject by measuring a signal of y-axis for a time $t_y$, and averaging the signal measured. The method further comprises, detecting the hand on which the subject carries the monitoring device by measuring a signal of the x-axis for a time $t_x$ and averaging the signal measured. The method also comprises, using the obtained information to optimise the activity monitoring, and further to determine a main axis of motion of the monitoring device and direction of the main axis of motion in order to improve recognition of the activity of the subject.

8 Claims, 6 Drawing Sheets

(56) References Cited

U.S. PATENT DOCUMENTS

| | | | |
|---|---|---|---|
| 2005/0119036 A1* | 6/2005 | Albanna | G06F 1/00 463/7 |
| 2011/0109329 A1 | 5/2011 | Diebold et al. | |
| 2016/0262685 A1* | 9/2016 | Wagner | A61B 5/1101 |
| 2016/0349803 A1* | 12/2016 | Dusan | G04C 3/002 |
| 2017/0007166 A1* | 1/2017 | Roovers | G01C 22/002 |

FOREIGN PATENT DOCUMENTS

| | | | |
|---|---|---|---|
| WO | 2015122879 A1 | 8/2015 | |
| WO | WO-2015128226 A1 * | 9/2015 | G01C 22/002 |

\* cited by examiner

METHOD FOR MONITORING ACTIVITY OF SUBJECT AND MONITORING DEVICE THEREFOR

TECHNICAL FIELD

The present disclosure relates generally to activity monitoring, and, more specifically, to a method for monitoring activity of a subject and a monitoring device therefor.

BACKGROUND

Recent consumer's interest in personal health has led to a variety of personal health monitoring devices being offered in the market. Many of these monitoring devices can be worn on finger, wrist or some other body part. These body-worn ("wearable") monitoring devices are well known in the art and are used to detect motion and position, and to infer physiological parameters and caloric expenditure therefrom. Such wearable monitoring devices, generally, include some electronic elements, such as flexible printed circuit board, processor, sensor, battery, and motion sensors. The motion sensor is typically or a combination of an accelerometer which is sensitive to linear or angular acceleration and also to earth gravity and their direction, or a magnetometer which is sensitive to detecting the magnetic field of earth and surrounding environment, and a gyroscope which is sensitive to detecting angular velocity.

It may be contemplated that these monitoring devices, whether in form of a ring or a wristband, can respectively be placed on a finger or a wrist in two orientations, in general, with respect to its edges. Since motion and position detection is based on orientation of the monitoring device, it is important to know which axis and along which direction, the motion sensor is most sensitive and useful for detection of motion or non-motion during use. Further, since hand motions are symmetric over the centre line seeing from the front of the body, but the motions are not symmetric over the centre line seeing from side of the body, it is important to know in which hand (left-hand or right-hand) the monitoring device has been placed. This correct orientation and placement data can be used for more accurate motion analysis, for example, a hand motion from the side to the front during walking can be valued higher when it is known that which hand is moving at this way.

A current solution is to compensate the problem of these different positions of the monitoring devices, by using a common 3D motion algorithm which combines x, y and z axes signals using squares, i.e., a sum vector of three motion sensor axis signals. This direction independent algorithm may work fine for step and activity counting, but cannot provide more accurate motion detection, motion recognition, and calorie counting which are based on separate axis signal detection. Therefore, when using an axis specific motion detection and classification, it is important to know how the monitoring device is oriented and placed with respect to the subject's body. To do this without asking an end user to input this information, which is an avoidable inconvenience, it is required to automatically detect the orientation and placement of the monitoring device.

Therefore, in light of the foregoing discussion, there exists a need to overcome the aforementioned drawbacks of the conventional monitoring devices for improving activity monitoring of the subject.

SUMMARY

The present disclosure seeks to provide a method for monitoring activity of a subject.

The present disclosure also seeks to provide a monitoring device for monitoring activity of a subject.

In one aspect, an embodiment of the present disclosure provides method for monitoring activity of a subject by means of a monitoring device, wherein the monitoring device is arranged to be carried on a finger of a hand or on a wrist of an arm and comprising an element indicating a pre-defined position for carrying the device, has a first edge side, a second edge side, an inner surface and an outer surface, and comprises at least one accelerometer configured to sense acceleration of gravity along at least an x-axis and a y-axis, the accelerometer being arranged on the monitoring device in such a manner that the y-axis is the axis passing though the device from the first edge side to the second edge side and parallel to the inner surface of the device, a signal of the y-axis is defined to have a first sign in the direction that has a greater acceleration of gravity, and the signal of the y-axis is defined to have a second sign in the direction opposite the direction of the first sign, the method comprising detecting the direction of the device with respect to the hand of the subject by measuring a signal of the y-axis for a time $t_y$ and averaging the signal measured, wherein the first edge side of the monitoring device is directed towards a distal end of the finger or the arm, when the average signal of the y-axis is of the first sign, and the first edge side of the monitoring device is directed towards a body end of the finger or the arm, when the average signal of the y-axis is of the second sign, using the obtained information to optimise the activity monitoring.

In another aspect, an embodiment of the present disclosure provides a monitoring device for monitoring activity of a subject, wherein the monitoring device is arranged to be carried on a finger of a hand or on a wrist of an arm and comprises an element indicating a pre-defined position for carrying the device; has a first edge side, a second edge side, an inner surface and an outer surface; and comprises a processing unit and at least one accelerometer configured to sense acceleration of gravity along at least an x-axis and a y-axis, the accelerometer being arranged on the monitoring device in such a manner that the y-axis is the axis passing though the device from the first edge side to the second edge side and parallel to the inner surface of the device, a signal of the y-axis is defined to have a first sign in the direction that has a greater acceleration of gravity, the signal of the y-axis is defined to have a second sign in the direction opposite the direction of the first sign, the x-axis is perpendicular to the y-axis and parallel to a tangent of the inner surface of the device at the element indicating the pre-defined position, the signal of the x-axis is defined to have a first sign in the direction that has a greater acceleration of gravity when the device is placed on a horizontal surface in a position where the outer surface of the device is facing the horizontal surface, the outer surface of the element indicating the pre-defined position is directed upwards, such that a tangent of the outer surface of the element in the middle of the element is parallel to the horizontal surface, whereafter the device has been turned 90° counter clock wise, such that the outer surface of the device remains facing the horizontal surface and the tangent of the outer surface of the element in the middle of the element is perpendicular to the horizontal surface, and the processing unit being configured to detect the direction of the device with respect to the hand of the subject by measuring a signal of the y-axis for a time $t_y$ and averaging the signal measured, wherein the first edge side of the monitoring device is directed towards a distal end of the finger or the arm, when the average signal of the y-axis is of the first sign, and the first edge side of the monitoring device is directed towards a body end of the finger or the arm, when the average signal of the y-axis is of the second sign.

Embodiments of the present disclosure substantially eliminate or at least partially address the aforementioned problems in the prior art, and enables improvement in monitoring of the activity of the subject.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
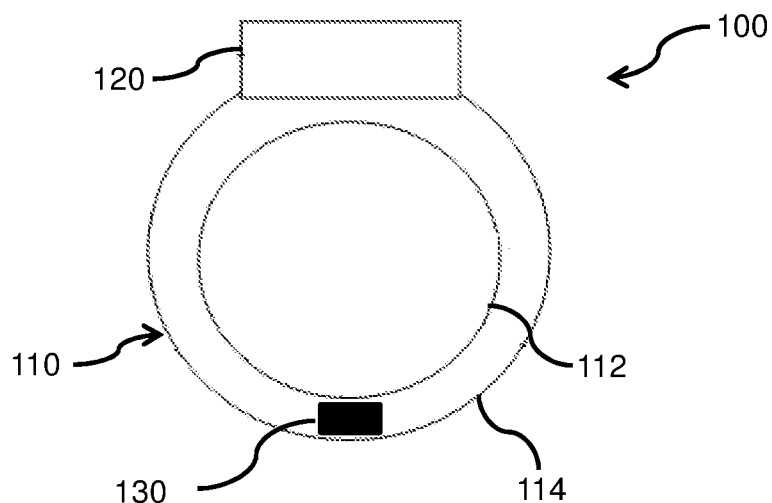
FIG. 1 is a schematic side view of a monitoring device, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides method for monitoring activity of a subject by means of a monitoring device, wherein the monitoring device is arranged to be carried on a finger of a hand or on a wrist of an arm and comprising an element indicating a pre-defined position for carrying the device, has a first edge side, a second edge side, an inner surface and an outer surface, and comprises at least one accelerometer configured to sense acceleration of gravity along at least an x-axis and a y-axis, the accelerometer being arranged on the monitoring device in such a manner that the y-axis is the axis passing though the device from the first edge side to the second edge side and parallel to the inner surface of the device, a signal of the y-axis is defined to have a first sign in the direction that has a greater acceleration of gravity, and the signal of the y-axis is defined to have a second sign in the direction opposite the direction of the first sign, the method comprising detecting the direction of the device with respect to the hand of the subject by measuring a signal of the y-axis for a time $t_y$ and averaging the signal measured, wherein the first edge side of the monitoring device is directed towards a distal end of the finger or the arm, when the average signal of the y-axis is of the first sign, and the first edge side of the monitoring device is directed towards a body end of the finger or the arm, when the average signal of the y-axis is of the second sign, using the obtained information to optimise the activity monitoring.

In another aspect, an embodiment of the present disclosure provides a monitoring device for monitoring activity of a subject, wherein the monitoring device is arranged to be carried on a finger of a hand or on a wrist of an arm and comprises an element indicating a pre-defined position for carrying the device; has a first edge side, a second edge side, an inner surface and an outer surface; and comprises a processing unit and at least one accelerometer configured to sense acceleration of gravity along at least an x-axis and a y-axis, the accelerometer being arranged on the monitoring device in such a manner that > the y-axis is the axis passing though the device from the first edge side to the second edge side and parallel to the inner surface of the device,
> a signal of the y-axis is defined to have a first sign in the direction that has a greater acceleration of gravity,
> the signal of the y-axis is defined to have a second sign in the direction opposite the direction of the first sign,
> the x-axis is perpendicular to the y-axis and parallel to a tangent of the inner surface of the device at the element indicating the pre-defined position,
> the signal of the x-axis is defined to have a first sign in the direction that has a greater acceleration of gravity when the device is placed on a horizontal surface in a position where the outer surface of the device is facing the horizontal surface,
> the outer surface of the element indicating the pre-defined position is directed upwards, such that a tangent of the outer surface of the element in the middle of the element is parallel to the horizontal surface, whereafter
> the device has been turned 90° counter clock wise, such that the outer surface of the device remains facing the horizontal surface and the tangent of the outer surface of the element in the middle of the element is perpendicular to the horizontal surface, and the processing unit being configured to > detect the direction of the device with respect to the hand of the subject by measuring a signal of the y-axis for a time $t_y$ and averaging the signal measured, wherein
> the first edge side of the monitoring device is directed towards a distal end of the finger or the arm, when the average signal of the y-axis is of the first sign, and
> the first edge side of the monitoring device is directed towards a body end of the finger or the arm, when the average signal of the y-axis is of the second sign.

The monitoring device of the present disclosure specifically optimises the activity monitoring of the subject. The term "activity monitoring" used herein refers to the measurement of one or a plurality of physiological properties related to the physical activity and related energy expenditure of the subject. The data about the physical activity of the subject can be used to determine the state of his or her health. This information about the physical activity can assist the individual in maintaining or improving his or her functional health status and quality of life. The term "subject" used herein is in reference to a human being, although it would be understood that such a monitoring device can be applied for any object for motion detection or motion recognition.

The monitoring device is the form of a ring arranged to be carried on a finger, such as an index finger, of a hand of the subject. However, it may be evident to those skilled in the art that the monitoring device may be in the form of any other wearable, such as a band adapted to be worn on a wrist of an arm, or any suitable body part of the subject, from where at least one position and motion data of the subject can be measured. In such instance, the monitoring device may be configured to have a size to be suitably worn at such body parts of the subject. For the purpose of the present disclosure, herein afterwards, the monitoring device has been described in reference to a ring arranged to be carried on the finger of the subject.

In an example, the monitoring device comprises a body part having a first edge side, a second edge side, an inner surface and an outer surface. The said edge sides and the said surfaces may be contemplated to have their usual meaning and further have been described later with reference to figures for better understanding. The monitoring device may include at least one cavity having a depth, which is arranged on the inner surface of the body part. The body part, for the monitoring device, may be made of a mouldable ceramic material, such as selected from a group consisting of zirconium, aluminium nitride, aluminium oxide, Boron carbide, silicon carbide, silicon nitride, titanium diboride and yttrium oxide. Alternatively, non-ceramic material, such as plastic, metal, rubber or any combination thereof may be used for forming the melded body part. The monitoring device may include an electronic part arranged in the said cavity, in which the electronic part has a thickness that is less than the depth of the cavity to be arranged therein. The monitoring device may further include a coating made of an epoxy material on the inner surface of the body part, covering the electronic part and the cavity.

According to an embodiment, the monitoring device includes an element indicating a pre-defined position for carrying it. In an example, the said element may be a stone or some marking which can be identified as a reference for direction/orientation of the monitoring device, when worn on the finger of the subject. It may be understood that the pre-defined position may be any reference which can be used to distinguish between the first edge side and the second edge side of the monitoring device. The element in the physical form, such as a stone, may be arranged on the outer surface of the monitoring device. The terms "element" and "stone" have been interchangeably used hereinafter. It is also possible that the marking is invisible to the user, but the electronics and especially the sensing element has two recognizable directions.

The stone may be shaped to have distinguishable ends, an upper end and a lower end. The stone with distinguishable ends provides the benefit that it may be seen in a traditional manner, and thus the wearer may be able to identify which edge side, i.e. the first edge side or the second edge side, of the monitoring device is placed in the direction of a distal end or a body end relative to the finger, in which the monitoring device is worn.

According to an embodiment, the method and system may comprise the possibility for the user to enter information about which hand is his/her dominant hand. Indeed, typically the dominant hand is more active than non-dominant hand in many activities, such as writing, household chores, etc. By combining the information about which hand is dominant and the detected hand on which the device is worn, lower factors can be applied in calorie and step counting in light intensity activities. For example, different function on the x-, y- and z-axis can be selected depending on the hand the device is worn and the position on which the device is worn, so that movements or series of movements that do not represent a whole body activity are less pronounced and vice versa. For example, type writing, piano playing or dish washing can then be detected and treated as no more than activity with a light intensity.

It may be contemplated that the monitoring device in the form of the ring could distinguishably be placed on the finger in eight (8) ways. Similarly, the monitoring device in the form of the wrist band device also has the same basic eight positions. Further, since the monitoring device can be turned over the finger or the wrist, the monitoring device possibly has infinite number of positions between these eight positions. These positions are primarily distinguishable in view of the placement of the monitoring device either over a left hand or a right hand of the subject, the element being positioned either on the back or palm side of the hand, and the element's upper/lower end towards or away from a distal end of fingers, in which the monitoring device is worn. These eight positions can be classified as:

When the monitoring device is worn on the left-hand finger
 the stone towards the back of the hand AND the stone's upper end towards the distal end of the finger (marked as L-B-U=LEFT-BACK-UPPER)
 the stone towards the back of the hand AND the stone's lower end towards the distal end of the finger (marked as L-B-L=LEFT-BACK-LOWER)
 the stone towards the palm of the hand AND the stone's upper end towards the distal end of the finger (marked as L-P-U=LEFT-PALM-UPPER)
 the stone towards the palm of the hand AND the stone's lower end towards the distal end of the finger (marked as L-P-L=LEFT-PALM-LOWER)

To set the ring into right hand finger
 the stone towards the back of the hand AND the stone's upper end towards the distal end of the finger (marked as R-B-U=RIGHT-BACK-UPPER)
 the stone towards the back of the hand AND the stone's lower end towards the distal end of the finger (marked as R-B-L=RIGHT-BACK-LOWER)
 the stone towards the palm of the hand AND the stone's upper end towards the distal end of the finger (marked as R-P-U=RIGHT-PALM-UPPER)
 the stone towards the palm of the hand AND the stone's lower end towards the distal end of the finger (marked as R-P-L=RIGHT-PALM-LOWER)

All the above mentioned cases are possible, but the stone on the palm side is generally not obvious in normal use. Therefore, the solutions provided in the present disclosure focus on the cases where the stone is on the back side of the hand (L-B-U, L-B-L, R-B-U, R-B-L). It may be contemplated by a person skilled in the art that the corresponding solution can be presented to the cases when the stone of the monitoring device is on the palm side of the hand, and thus have not been described for the brevity of the disclosure.

The monitoring device arranged in a three-dimensional (3D) space may be referenced by means of Cartesian coordinate system, i.e. in terms of three orthogonal axes, x-axis, y-axis, and z-axis. With reference to a subject's hand, these directions are formed "antero-posterior", "medio-lateral" and "vertical", that are denoted as x, y and z, respectively. The three orthogonal axes may be imagined according to the "right hand rule", in which the first or index finger, the second finger or palm and the thumb of a right-hand are arranged orthogonal to each other; the x-axis can be imagined to be along the first or the index finger, the y-axis can be imagined to be along the second finger or the palm, and the z-axis can be imagined to be along the direction of the thumb. For the purpose of the present disclosure, the y-axis is the axis passing though the said body of the monitoring device, from the first edge side to the second edge side, and parallel to the inner surface of the monitoring device. Further, the x-axis is perpendicular to the y-axis and parallel to the tangent of the inner surface of the monitoring device at the element indicating the pre-defined position. Further, the z-axis may be considered the axis perpendicular to the plane formed between the x and y axes.

The monitoring device is configured to measure user's movements and position data. For this purpose, the monitoring device includes at least one motion sensor. Using modern fabrication techniques, the motion sensor can be built small and lightweight, and be integrated into the body of the monitoring device. For example, the motion sensor may be disposed in the said cavity formed between the inner surface and the outer surface of the body of the monitoring device. Thus, the monitoring device can be worn for a long period of time without causing any burden to the subject wearing it.

In one example, the motion sensor is selected from the group consisting of an accelerometer, a gyroscope and a magnetometer (magnetic field sensor). The motion sensor, in the form of the accelerometer, is sensitive to linear or angular acceleration and also to earth gravity and their direction, and uses this principle for detecting the direction of motion of the monitoring device. The motion sensor, in the form of the gyroscope, is sensitive to and detects angular velocity, and uses this principle for detecting the direction of motion of the monitoring device. The motion sensor, in the form of the magnetometer, is sensitive to and detects the magnetic field of earth and surrounding environment, and uses this principle for detecting the direction of motion of the monitoring device. The motion sensor may further be a combination of two or more of the accelerometer, the gyroscope and the magnetic field sensor. For further reference, the motion sensor has been described in terms of the accelerometer; however it will be readily appreciated that the accelerometers are merely preferred motion sensors, and that any other described motion sensors could be used in an embodiment and achieve the advantages of the present disclosure.

In an embodiment, the monitoring device includes at least one accelerometer configured for monitoring activity of the subject by measuring movements and positions of the monitoring device as it moves along with the motion of the hand of the subject. The accelerometers may include strips of piezo-electric material that is uni-axial and serial bimorph. The strips are fixed at one end thereof. The piezo-electric accelerometers act as damped mass-spring systems, i.e. the piezo-electric strips act as spring and damper. Movements of the strips due to movement of the individual generate an electric charge leading to a measurement of a data signal. Typically, the monitoring device includes three accelerometers (3-axis accelerometer) which are arranged in mutually orthogonal directions, i.e., x, y and z axes. The accelerometers output data signals which are indicative of the respective accelerations experienced by the orthogonally disposed accelerometers.

In one embodiment, the accelerometer is configured to sense acceleration of gravity along at least the x-axis and the y-axis. The accelerometer is arranged on the monitoring device in such a manner that the signal of the y-axis is defined to have a first sign in the direction that has a greater acceleration of gravity. Further, the signal of the y-axis is defined to have a second sign in the direction opposite the direction of the first sign of the y-axis. Also, the signal of the x-axis is defined to have a first sign in the direction that has a greater acceleration of gravity when the monitoring device is placed on a horizontal surface in a position where the outer surface of the monitoring device is facing the horizontal surface, the element indicating the pre-defined position is directed perpendicularly upwards and the device is turned 90° counter clock wise, i.e. to the left when seen from the user's perspective. Further, the signal of the x-axis is defined to have a second sign in the direction opposite the direction of the first sign of the x-axis. A motion sensor can be placed in any direction in the device. The sensor can thus monitor x-, y- and z-axis related to its own coordination. The sensor itself or the application software can translate the sensor coordinates to resemble the x- and y-axis as described in this description.

The monitoring device may also include other electronic components configured to collect and analyse motion sensors data (i.e. raw data). For example, the monitoring device may include, but not limited to, a controller, a processing unit, a memory and a communication module. The controller is operable to control operation of the motion sensors for generating data related to the movement of the subject. The processing unit may be operable to process or analyse collected data generated by the motion sensors. Further, the memory is used for storing the analysed or processed data. Moreover, the communication module is configured to establish a communication between the monitoring device and a mobile communication device.

In an example, the mobile communication device may be configured to communicate with the monitoring device, using a communication module. For example, the mobile communication device may be wirelessly connected to the monitoring device by a wireless connection such as a Wi-Fi, Bluetooth and the like. Further, the mobile communication device comprises a computing device which includes, but not limited to, a smart phone, a tablet computer, a phablet and a laptop. The mobile communication device is configured to collect the raw data from the monitoring device. Further, the mobile communication device is operable to perform data analysis of such raw data. It is to be understood that the mobile communication device includes required electronic elements, such as a processor, and algorithms to perform such data analysis. The data analysis may include determining or deriving various aspects associated with the physical activity of the subject. Further, a server is configured to communicate with the mobile communication device. For example, the server is communicatively coupled to the mobile communication device through a communication network which can be wired, wireless or a combination thereof. For example, the communication network includes, but is not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, and Worldwide Interoperability for Microwave Access (WiMAx) networks.

It may be understood that since the monitoring device is attached to the finger of the subject, as the subject may perform various operations with his hands, the subject's hand, or particularly the finger in which the monitoring device is worn may change its orientation number of times. However, it has been found that human beings keep their hands in the orientation/position such that, most of the time the distal end of the finger is lower than body end of the finger. This can be easily imagined for the situations when a human being is in standing position, walking, or the like. Further it may be imagined that this is also valid for most common sitting positions, as the finger-tip is, most of the times, hanging a little bit downward. Also it may be imagined that during sleep, usually, the hand is kept so that the fingertip is facing downward. So it may be assumed that for most of the natural positions for the human beings, the distal end of the finger is generally lower than body end of the finger. Naturally there are some moments and activities when a fingertip is upward, such as, when the person is lifting a weight above his head, or the like, but these situations are rather short periods, and therefore can be safely ignored for purpose of the present disclosure. Further, the present disclosure provides averaging means (described below) which can compensate for these short orientation changes for more accurate activity monitoring.

In an embodiment, the monitoring device of the present disclosure is configured to determine its orientation and placement with respect to the subject's body, in which it is worn. For this purpose, the processing unit associated with the motion sensor is configured to average the measured gravity signal along y and x axes for a certain time period '$t_y$' and '$t_x$', respectively, to cancel out any spurious signals due to insignificant orientation changes of the monitoring device, and thus in order to better predict the orientation and placement of the monitoring device. In one example, one suitable monitoring time period for '$t_y$' and '$t_x$' is 30 seconds. However, it may be contemplated that any time period may be defined for such purpose based on the requirements and conditions for activity monitoring. In another example, y-axis and x-axis monitoring can be done for any time '$t_y$' and '$t_x$' between 1 second to 3600 seconds, or more. In a preferred example, y-axis and x-axis monitoring is averaged for a period '$t_y$' and '$t_x$' ranging between 30-180 seconds, as it has been found to give reliable results. The said time period of 20-180 seconds makes the measurement neither too fast nor too slow, and thus provides a good estimate for any compensation. In another example, successive time periods '$t_y$' and '$t_x$' can be further averaged and be used for voting with different coefficients, as would be contemplated by a person skilled in the art.

By calculating how much the y-axis signal (the axis along the finger) is of the first sign or the second sign (can be considered as positive and negative, respectively), the direction of orientation of the monitoring device can be defined. It may be contemplated by a person skilled in the art that the signs of the readings of the accelerometer only along y-axis, i.e. the axis which is along the finger, are required to be measured and analyzed for determining the orientation of the monitoring device with respect to the finger. Also it may be understood that the amplitude of the signal along the y-axis may not affect the calculation for determination of the orientation of the monitoring device. Further it may be understood that this set of rules for determination of the orientation of the monitoring device may be independent of the condition, whether the monitoring device is worn on the left-hand or the right-hand.

In one configuration of the monitoring device, if the signal of the y-axis is most of the time of the first sign (positive), it may be determined that the upper end of the element is towards the distal end of the finger. Further, for the same configuration, if the signal of the y-axis is most of the time of the second sign (negative), it may be determined that the upper end of the element is towards the body end of the finger. The same configuration of the monitoring device is considered for further calculations and description of the embodiments of the present disclosure.

In one example, if the subject is in motion, then there will be other movements which cause extra acceleration signals by the accelerometer. To confirm these extra movements, the linear acceleration signals are summed up using a sum vector, $H=\sqrt{(x^2+y^2+z^2)}$. If the calculated value for the signal H is greater than 1 (1G, where 'G' is the acceleration due to gravity), then it may be established that there are acceleration signals other than the earth gravity; as with only the earth gravity acting on the monitoring device, the maximum amplitude of the signal along y-axis could be 1. So the time period during which the said value for the signal H stays greater than '1' can be skipped from the direction analysis.

In an embodiment, the monitoring device of the present disclosure is further configured to determine its placement in respect of the hands of the subject's body, i.e., whether it is placed on the left-hand or the right-hand. For this purpose, the following set of rules may be employed:

When the monitoring device is placed to the finger so that the upper end of the element is towards the distal end of the finger, i.e., the measured signals along the y-axis is of first sign (positive), then If x-axis signal is of the first sign (positive), the monitoring device is determined to be placed on the left-hand, and If x-axis signal is of the second sign (negative), the monitoring device is determined to be placed on the right-hand, and When the monitoring device is placed to the finger so that the upper end of the element is towards the body/wrist end of the finger, i.e., y-axis is of the second sign (negative), then If x-axis signal is of the first sign (positive), the monitoring device is determined to be placed on the right-hand, and In an embodiment, the processing unit of the monitoring device is further configured to reduce/eliminate noise in the signals along the x-axis and the y-axis by comparing the values of the signals with a pre-determined threshold value. When the calculated average signals are analyzed, these signals are first compared to the threshold value. The threshold value can be zero (0), or in some cases it can be set to a value above the noise level, for example 50 mG or 0.05 G (where 'G' is the acceleration due to gravity). Typically, the threshold value is a range of values, for example, in above case, −50 mG to +50 mG. In such cases, it may be contemplated by a person skilled in the art that the orientation/position of monitoring device is only determined if the values for the y and x signals are lower or above the corresponding threshold value, i.e., the values are either greater than a positive limit of the threshold value and lower than a negative limit of the threshold value, as the output of the determination cannot be considered reliable otherwise. In other words, the detection of the hand on which the subject carries the device is carried out if the absolute value of the average signal of the x-axis exceeds the pre-determined threshold value.

In an embodiment, the method of the present disclosure may be implemented using a plurality of pseudo codes, and one such example pseudo code includes:

```
% DEFINE THE RING POSITION 1=y-L, 2=y-R, 3=y+L, 4=y+R, 0=Undetermined
if y -signal < -THD,
    if x-signal > THD,
        directions = 1; % STONE UPPER to BODY, LEFT HAND (L-L)
    else if x-signal < -THD,
        directions = 2; % STONE UPPER to BODY, RIGHT HAND (R-L)
    else
        directions = 0; % Undetermined
    end
else if y-signal > THD,
    if x-signal > THD,
        directions = 4; % STONE UPPER to DISTAL, RIGHT HAND (R-U)
    else if x-signal < -THD,
        directions = 3; % STONE UPPER to DISTAL, LEFT HAND (L-U)
    else
        directions = 0; % Undetermined
    end
else
    directions = 0; % Undetermined
end
```

If x-axis signal is of the second sign (negative), the monitoring device is determined to be placed on the left-hand.

It may be contemplated that the above set of rules are implemented under the assumption that the monitoring device is placed such that the back side of the subject's hand is outwards of the subject's body (or the palm side of the hand is inwards to the body), which is dominantly the case for most regular positions of the subject's body.

Again, for this purpose, the processing unit associated with the motion sensor is configured to average the measured x-axis signals for a certain time period to cancel out any spurious signals due to insignificant orientation changes of the monitoring device, and thus in order to better predict the placement of the monitoring device with respect to the subject's hand. The process and exemplary time values has been described in terms of calculation for signals of y-axis, and the same methodology can be employed here, and thus have not been described in detail for the brevity of the disclosure.

The above example pseudo code is implemented for both the determination of the orientation of the monitoring device with respect to the subject's finger to which it is worn, i.e., upper/lower end of the element towards the distal end or the body end; and further for determining the placement of the monitoring device with respect to the subject's hands to which it is worn, i.e., left-hand or right-hand.

The present disclosure provides a method for monitoring activity of a subject by means of a monitoring device. The present disclosure takes into consideration if the monitoring device is placed on the left-hand or the right-hand (placement of the monitoring device), and which side of the monitoring device is towards the body end and which side is towards the finger-tip (orientation of the monitoring device), when the monitoring device, say in the form of a ring is worn on the finger of the subject. As the data from the motion sensor is used for activity monitoring of the subject, it makes big difference how the data of different sensor axis is used and analyzed. Different kind of hand movements are related to different kind of body movements. So certain hand movements can be valued differently when counting energy consumption based on the motion data. For example, the subject's body is not expected to consume so much energy when detecting that moving hand on the side of the body (z-axis) compared to that when a forward hand movement is detected, with the same motion sum signal as employed with the existing technologies.

The detection is based on an accelerometer signal and typical use regular positions, such as hanging hand is pointing down, or during walking the hand moves side and front, to determine the orientation and placement information of the monitoring device. This orientation and placement determination is helpful in determining a main axis of motion of the monitoring device and direction of the main axis of motion, which in turn is used for optimizing the measured signals for monitoring activity of the subject and motion recognition, by the monitoring device. Specifically, when the subject changes the orientation or the placement of the monitoring device, the measurements/analysis of the signals, by relevant motion sensors, are affected and often result in deviation, and thus incorrect readings for the monitored activity. The monitoring device of the present disclosure can eliminate this shortcoming by determining its exact orientation and placement and compensate for this deviation during analysis of the measured signals.

Therefore, with the monitoring device of the present disclosure, more accurate analysis can be achieved, resulting in better monitoring of the activity of the subject. The present monitoring device also enables to use only certain axis of the motion sensor for motion measurement, for example, the monitoring device can power OFF the accelerometer responsible for measurements along the second sign of signals for the z-axis (towards the body) when the monitoring device is determined to be placed on the left-hand and first sign of signals for the z-axis for the right-hand placement of the monitoring device, since the subject's hand do not show any significant movement in the directions along the said axes. This in turn helps to reduce energy consumption of the monitoring device, which is important since the monitoring device being of small size, could only accommodate a small battery to power up its electronic components, including motion sensors; and therefore increases the battery life of the monitoring device.

Since with the monitoring device of the present disclosure, its orientation and placement with respect to the body of the subject is known, it is also possible to recognize certain kinds/types of movements of the subject. For example, in a hypothetical case, the accelerometer indicates that there is a strong movement of about 0.8 G in the direction of the x-axis and also a movement of about 0.5 G in the direction of the y-axis. This combined with the knowledge that the monitoring device is on the right-hand and oriented away from the subject's body, it could be deduced that the subject is playing tennis and has forward hit the ball, the movement having a main axis that is between the x-axis and the y-axis. Thus the present monitoring device can provide better motion recognition which was not possible with the conventional monitoring devices.

DETAILED DESCRIPTION OF THE DRAWINGS

Referring to FIG. 1, illustrated is a schematic side view of a monitoring device 100, in accordance with an exemplary embodiment of the present disclosure. The monitoring device 100 includes a body part 110 and is configured to have a shape of ring that can be suitably worn on a finger of a subject (shown in subsequent figures). The body part 110 includes an inner surface 112 and an outer surface 114 opposite to the inner surface 112. The body part 110 may also include one cavity (not shown) having a depth and arranged on the inner surface 112 of the body part 110. Further, as shown, the monitoring device 100 includes an element 120 arranged on the outer surface 114 thereof.

The monitoring device 100 comprises a set of sensors, including motion sensors for measuring movements thereof. In an embodiment, the monitoring device 100 includes an accelerometer, schematically depicted in FIG. 1 and referenced by numeral 130.

Figure 2:
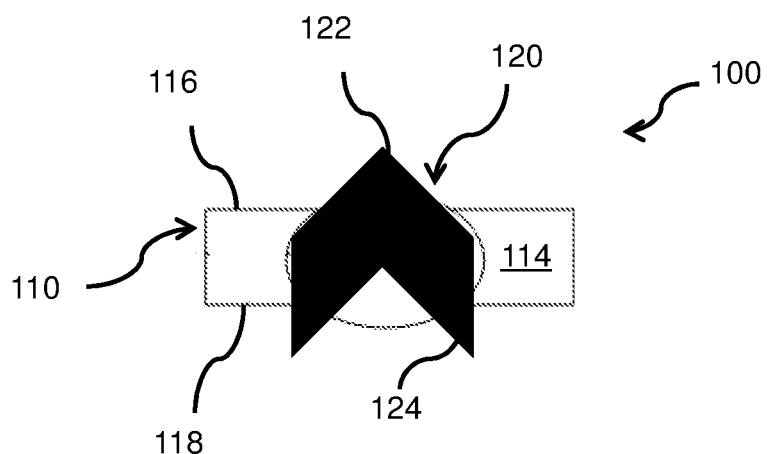
FIG. 2 is a schematic top view of the monitoring device, in accordance with an embodiment of the present disclosure.

Referring now to FIG. 2, illustrated is a schematic top view of the monitoring device 100, in accordance with an exemplary embodiment of the present disclosure. Specifically, FIG. 2 illustrates the body part 110, the element 120, and a first edge side 116 and a second edge side 118, of the monitoring device 100, disposed opposite to each other along the ends of the outer surface 114, as may be seen from the illustration. It may be noted that the shape of the element 120 is exemplary only, and has been illustrated in the manner in order to clearly differentiate between an upper end 122 and a lower end 124 of the element 120.

Figure 3:
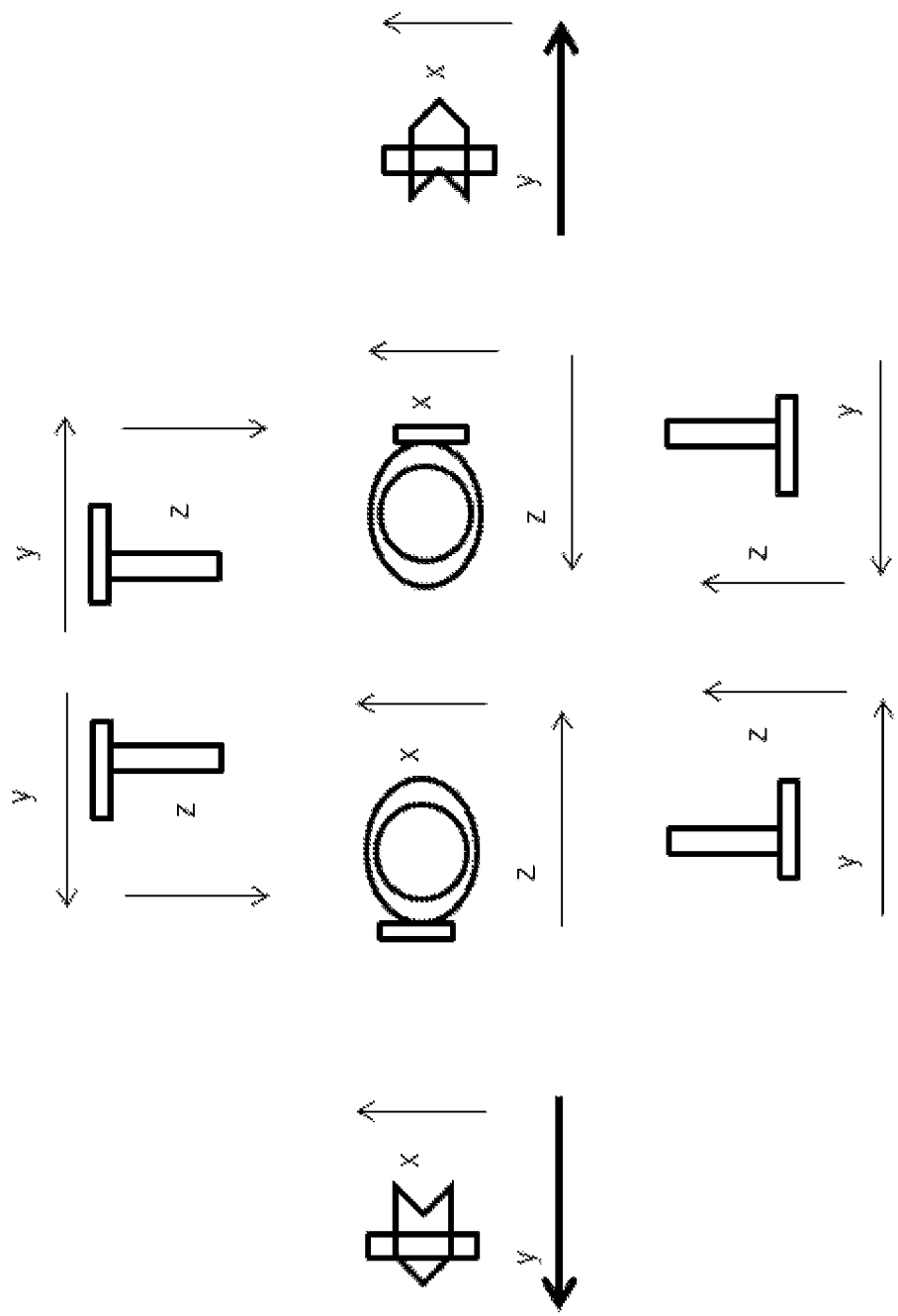
FIG. 3 is a schematic depiction of some of the possible positions of the monitoring device, in accordance with an embodiment of the present disclosure.

FIG. 3 schematically illustrates some of the possible positions of the monitoring device 100, as described above. As discussed, out of these possible positions of the monitoring device 100, four (4) prominent positions thereof, namely, R-B-U, R-B-L, L-B-U, and L-B-L are of major significance. These four prominent positions have been illustrated with reference to subject's body in FIGS. 4-7.

Figure 4:
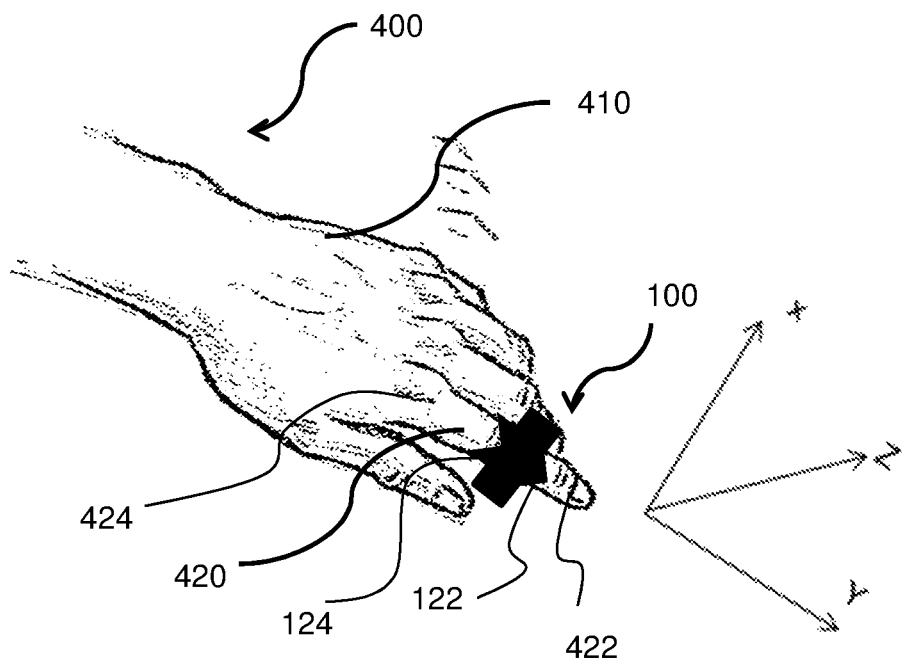
FIG. 4 is a perspective depiction of an arm of a subject with the monitoring device placed in a finger of a right-hand, in accordance with an embodiment of the present disclosure.

Referring now to FIG. 4, a right arm 400 extending with respect to a body (not shown), and a right hand 410 with the monitoring device 100 being worn on a finger 420 thereof, is depicted, in accordance with an exemplary embodiment of the present disclosure. A distal end 422 and a body end 424 of the finger 420 is marked for reference and understanding of the present disclosure. Further it may be seen that the upper end 122 of the element 120 (shown in FIG. 2) is towards the distal end 422 of the finger 420, and the lower end 124 of the element 120 is towards the body end 424 of the finger 420. It may be understood that the current FIG. 4 represents the R-B-U position, as defined above. In this position, as illustrated in FIG. 4, the signal of the y-axis is of the first sign (positive) and that of the x-axis is of the second sign (negative), which in turn can be used to infer that the monitoring device 100 is being worn on the right-hand 410 of the subject.

Figure 5:
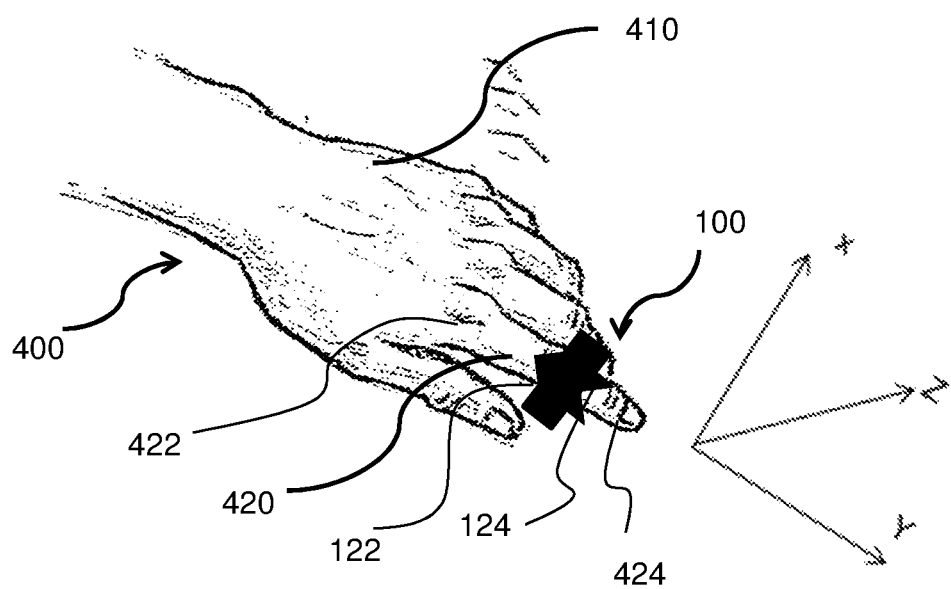
FIG. 5 is a perspective depiction of the arm of the subject with the monitoring device placed in the finger of the right-hand, in accordance with an embodiment of the present disclosure.
Figure 6:
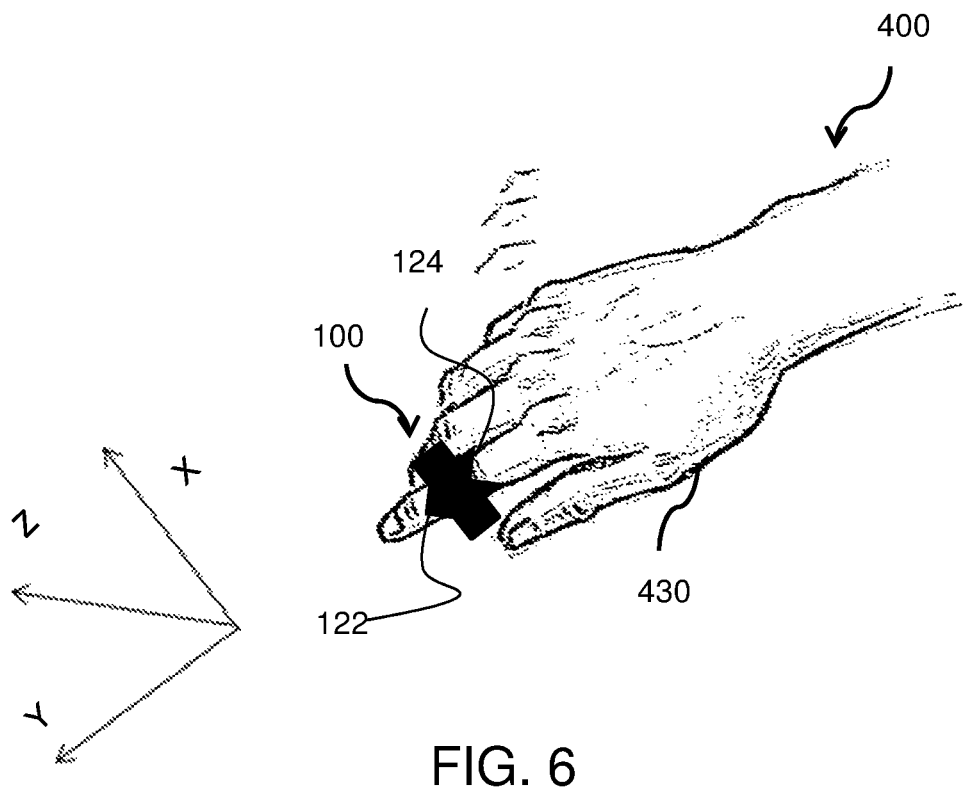
FIG. 6 is a perspective depiction of an arm of the subject with the monitoring device placed in a finger of a left-hand, in accordance with an embodiment of the present disclosure.
Figure 7:
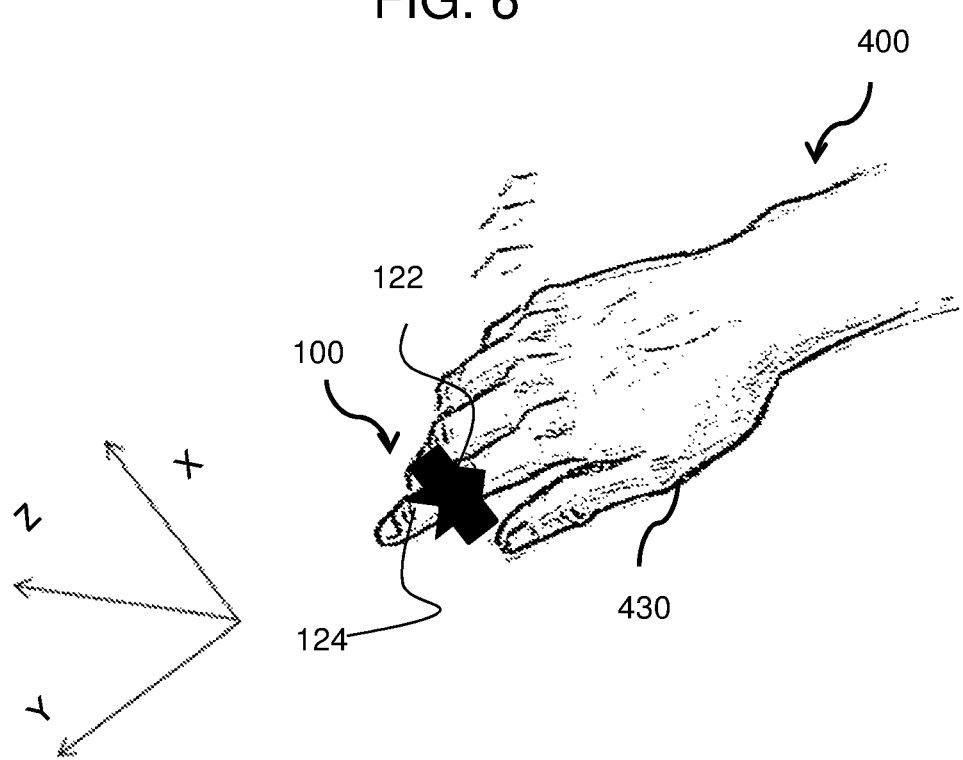
FIG. 7 is a perspective depiction of the arm of the subject with the monitoring device placed in the finger of the left-hand, in accordance with an embodiment of the present disclosure.

Similarly, FIGS. 5-7 illustrate the other three (3) prominent positions. For example, FIG. 5 illustrates the R-B-L position, in which the signal of the y-axis is of the second sign (negative) and that of the x-axis is of the first sign (positive), which in turn can be used to infer that the monitoring device 100 is being worn on the right-hand 410 of the subject. FIG. 6 illustrates the L-B-U position, in which the signal of the y-axis is of the first sign (positive) and that of the x-axis is also of the first sign (positive), which in turn can be used to infer that the monitoring device 100 is being worn on a left-hand 430 of the subject. FIG. 7 illustrates the L-B-L position, in which the signal of the y-axis is of the second sign (negative) and that of the x-axis is also of the second sign (negative), which in turn can be used to infer that the monitoring device 100 is being worn on the left-hand 430 of the subject.

Figure 8:
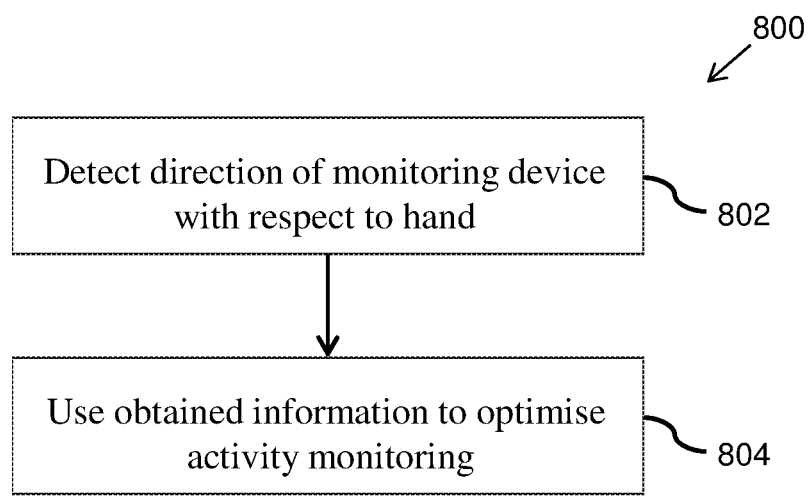
FIG. 8 is an illustration of steps of a method for monitoring activity of the subject by means of the monitoring device, in accordance with an embodiment of the present disclosure.

Referring now to FIG. 8, illustrated are steps of a method 800 for monitoring activity of the subject by means of the monitoring device 100, in accordance with an embodiment of the present disclosure.

At step 802, the method 800 includes detecting the direction of the monitoring device 100 with respect to the hands 410, 430 of the subject by measuring a signal of the y-axis for a time $t_y$ and averaging the signal measured.

At step 804, the method 800 includes using the obtained information to optimise the activity monitoring.

Figure 9A:
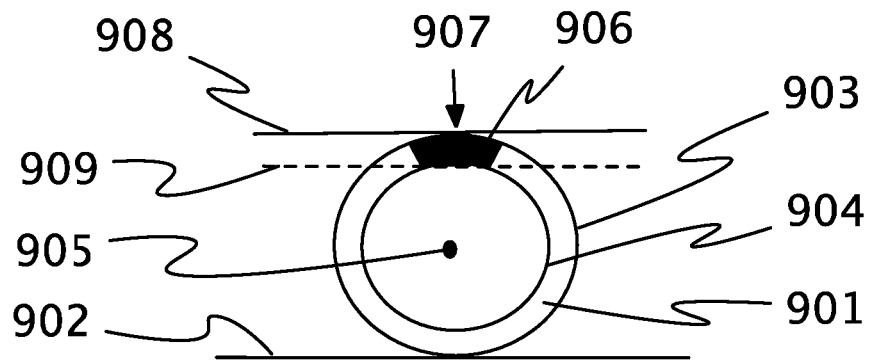
FIG. 9A to 9C are an illustration of the y- and x-axes as described in this description.
Figure 9B:
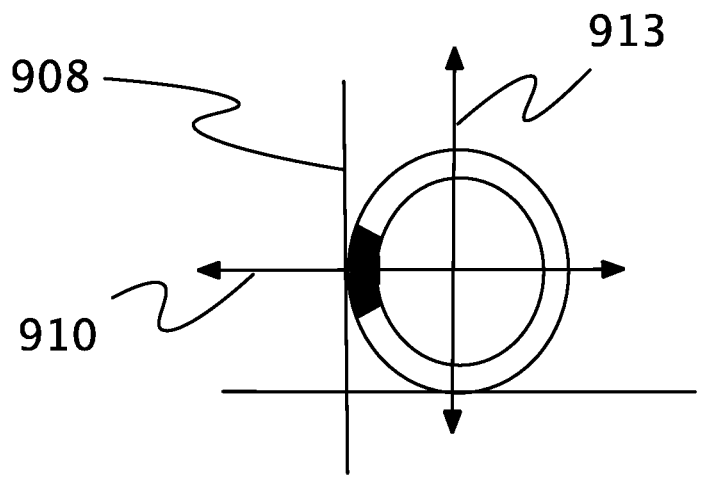
Figure 9C:
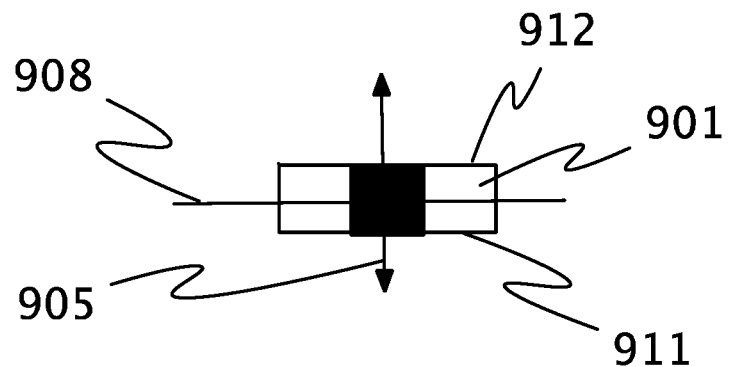

FIG. 9A to 9C are an illustration of the y- and x-axes as described in this description. In FIG. 9A, the device, in this case a ring 901 is arranged on a horizontal surface 902, and standing upright on it, i.e. the outer surface 903 of the ring is facing the horizontal surface. Also the inner surface 904 of the ring is shown. The view is thus a side view. The y-axis is the central axis of the ring, shown at 905. The element 906 indicating a pre-defined position for carrying the ring and its middle 907 are also shown, as well as a tangent 908 of the outer surface of the element at its middle and a tangent 909 of the inner surface of the ring. In this embodiment, the outer surface of the element is at the same level as the outer surface of the ring.

In FIG. 9B, the ring has been turned 90° to the left, i.e. counter-clock wise, while keeping the outer surface of the ring facing the horizontal surface. The x-axis 910 is thus shown, parallel to the horizontal surface, as well as a z-axis 913, which is perpendicular to both x- and y-axes. In FIG. 9C, the ring is shown as seen from the top, and the first edge side 911 as well as the second edge side 912 are illustrated.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for monitoring activity of a subject by means of a monitoring device,
wherein the monitoring device is arranged to be carried on a finger of a hand or on a wrist of an arm and comprising an element indicating a pre-defined position tor carrying the device,
has a first edge side, a second edge side, an inner surface and an outer surface, and
comprises at least one accelerometer configured to sense acceleration of gravity along at least an x-axis and a y-axis, the accelerometer being arranged on the monitoring device in such a manner
that the y-axis is the axis passing though the device from the first edge side to the second edge side and parallel to the inner surface of the device,
a signal of the y-axis is defined to have a first sign in the direction that has a greater acceleration of gravity, and
the signal of the y-axis is defined to have a second sign in the direction opposite the direction of the first sign,
the method comprising
detecting the direction of the device with respect to the hand of the subject by measuring a signal of the y-axis for a time ty and averaging the signal measured, wherein
the first edge side of the monitoring device is directed towards a distal end of the finger or the arm, when the average signal of the y-axis is of the first sign,
the first edge side of the monitoring device is directed towards a body end of the finger or the arm, when the average signal of the y-axis is of the second sign, and
using the obtained information to optimise the activity monitoring; and
the method further comprising detecting the hand on which the subject carries the device by measuring a signal of the x-axis for a time tx and averaging the signal measured, wherein
the x-axis is perpendicular to the y-axis and parallel to the tangent of the inner surface of the device at the element indicating the pre-defined position,
the signal of the x-axis is defined to have a first sign in the direction that has a greater acceleration of gravity when the device is placed on a horizontal surface in a position where the outer surface of the device is facing the horizontal surface,
the outer surface of the element indicating the pre-defined position is directed upwards, such that a tangent of the outer surface of the element in the middle of the element is parallel to the horizontal surface, whereafter the device has been turned 90° counter clock wise, such that the outer surface of the device remains facing the horizontal surface and the tangent of the inner surface of the device in the middle of the element is perpendicular to the horizontal surface,
the signal of the x-axis is defined to have a second sign in the direction opposite the direction of the first sign,
the monitoring device is worn on a right hand when the average signal of the y-axis and the average signal of the x-axis are of different signs, and
the monitoring device is worn on a left hand when the average signal of the y-axis and the average signal of the x-axis are of the same sign.

2. A method according to claim 1, further comprising using the obtained information for determining a main axis of motion of the monitoring device and direction of the main axis of motion in order to further optimise the activity monitoring.

3. A method according to claim 2, wherein only the main axis for motion is used for subsequent motion measurement.

4. A method according to claim 1, wherein the time ty and the time tx are independent of each other, and range between 1-3600 seconds.

5. A method according to claim 4, wherein the time ty and the time tx are independent of each other, and range between 20-180 seconds.

6. A method according to claim 1, wherein the detection of the hand on which the subject carries the device is carried out if the absolute value of the average signal of the x-axis exceeds a pre-determined threshold value.

7. A method according to claim 6, wherein the threshold value is 50 mG.

8. A monitoring device for monitoring activity of a subject, wherein the monitoring device is arranged to be carried on a finger of a hand or on a wrist of an arm and comprises an element indicating a pre-defined position for carrying the device; has a first edge side, a second edge side, an inner surface and an outer surface; and comprises a processing unit and at least one accelerometer configured to sense acceleration of gravity along at least an x-axis and a y- axis, the accelerometer being arranged on the monitoring device in such a manner that
the y-axis is the axis passing though the device from the first edge side to the second edge side and parallel to the inner surface of the device,
a signal of the y-axis is defined to have a first sign in the direction that has a greater acceleration of gravity,
the signal of the y-axis is defined to have a second sign in the direction opposite the direction of the first sign, the x-axis is perpendicular to the y-axis and parallel to a tangent of the inner surface of the device at the element indicating the pre-defined position, the signal of the x-axis is defined to have a first sign in the direction that has a greater acceleration of gravity when the device is placed on a horizontal surface in a position where the outer surface of the device is facing the horizontal surface, the outer surface of the element indicating the pre-defined position is directed upwards, such that a tangent of the outer surface of the element in the middle of the element is parallel to the horizontal surface, whereafter the device has been turned 90° counter clock wise, such that the outer surface of the device remains facing the horizontal surface and the tangent of the inner surface of the device in the middle of the element is perpendicular to the horizontal surface, and the processing unit being configured to detect the direction of, the device with respect to the hand of the subject by measuring a signal of the y-axis for a time ty and averaging the signal measured, wherein the first edge side of the monitoring device is directed towards a distal end of the finger or the arm, when the average signal of the y-axis is of the first sign, and the first edge side of the monitoring device is directed towards a body end of the finger or the arm, when the average signal of the y-axis is of the second sign and detect that the monitoring device is worn on a right hand when the average signal of the y-axis and the average signal of the x-axis are of different signs, and detect that the monitoring device is worn on a left hand when the average signal of the y-axis and the average signal of the x-axis are of the same sign.

* * * * *